United States Patent
Dai et al.

(10) Patent No.: US 12,226,240 B2
(45) Date of Patent: Feb. 18, 2025

(54) ALARM THRESHOLD SETTING SUGGESTION METHOD, SYSTEM AND MONITOR

(71) Applicant: SHENZHEN MINDRAY BIO-MEDICAL ELECTRONICS CO., LTD., Shenzhen (CN)

(72) Inventors: Jian Dai, Shenzhen (CN); Sanchao Liu, Shenzhen (CN); Zehui Sun, Shenzhen (CN); Wenyu Ye, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 445 days.

(21) Appl. No.: 17/394,320

(22) Filed: Aug. 4, 2021

(65) Prior Publication Data
US 2022/0039762 A1  Feb. 10, 2022

(30) Foreign Application Priority Data
Aug. 4, 2020  (CN) .......................... 202010774088.8

(51) Int. Cl.
  *A61B 5/00* (2006.01)
  *G08B 25/00* (2006.01)
  *G08B 29/18* (2006.01)

(52) U.S. Cl.
  CPC ............ *A61B 5/746* (2013.01); *G08B 25/008* (2013.01); *G08B 29/185* (2013.01)

(58) Field of Classification Search
  CPC ..... A61B 5/746; A61B 5/024; A61B 5/14542; A61B 5/7405; A61B 5/742; G08B 25/008;
(Continued)

(56) References Cited

U.S. PATENT DOCUMENTS

2017/0095217 A1    4/2017  Hubert et al.
2017/0235912 A1*   8/2017  Moturu .................. G16H 40/67
                                                    705/2
(Continued)

FOREIGN PATENT DOCUMENTS

CN    106228762 A    12/2016
CN    106456002 A    2/2017
(Continued)

OTHER PUBLICATIONS

Extended European Search Report issued in related European Application No. 21189676.6, mailed Jan. 5, 2022, 8 pages.
(Continued)

*Primary Examiner* — Quan Zhen Wang
*Assistant Examiner* — Rajsheed O Black-Childress
(74) *Attorney, Agent, or Firm* — BAYES PLLC (57) ABSTRACT

An alarm threshold setting suggestion method, a system and a monitor are provided in the disclosure. The method includes: obtaining monitoring data of a patient, determining whether the current alarm threshold associated with a monitoring parameter needs to be adjusted or not according to the monitoring data, and if yes, generating threshold setting suggestion information according to the monitoring data and the current alarm threshold associated with the monitoring parameter; and outputting the threshold setting suggestion information. In this way, not only is the user prompted to adjust the alarm threshold, but also the threshold setting suggestion information is provided for user reference, which are beneficial to relieving the problem of alarm fatigue.

18 Claims, 1 Drawing Sheet

(58) Field of Classification Search
CPC ...... G08B 29/185; G16H 40/63; G16H 40/67; G16H 50/20
See application file for complete search history.

(56) References Cited

U.S. PATENT DOCUMENTS

2018/0008207 A1* 1/2018 Sarkela .................. G16H 40/67
2018/0303413 A1* 10/2018 Hassan .................. G16H 40/67
2019/0295696 A1   9/2019 Yang et al.

FOREIGN PATENT DOCUMENTS

WO   2016099519 A1   6/2016
WO   2020132799 A1   7/2020

OTHER PUBLICATIONS

First Office Action issued in related Chinese Application No. 20201774088.8, mailed Dec. 25, 2024, 12 pages.

* cited by examiner

ALARM THRESHOLD SETTING SUGGESTION METHOD, SYSTEM AND MONITOR

CROSS-REFERENCE TO RELATED APPLICATIONS

This application claims benefits of priority to Chinese Application No. 202010774088.8, filed Aug. 4, 2020, which is incorporated herein by reference in its entirety.

TECHNICAL FIELD

The disclosure relates to the field of medical instruments, and in particular to an alarm threshold setting suggestion method, a system and a monitor.

BACKGROUND

A monitoring device is connected to a patient and configured to monitor physiological parameters of the patient, and if the physiological parameters monitored by the monitoring device exceed a preset threshold range during use of the monitoring device, the monitoring device sends out an alarm to indicate the physiological condition of the patient to a caregiver at this moment. However, in some cases, for example, due to differences in patients' diseases or differences in the normal physiological parameters of each patient, the monitoring parameters may frequently exceed preset thresholds, such as fluctuating around the thresholds, although the patient's condition at this moment is still normal or does not reach the point where an alarm is required to alert the caregiver. As a result, the caregiver cannot distinguish a truly clinically significant alarm and a non-clinically significant alarm in such frequent alarms, and thus a large number of insignificant alarms cause the problem of alarm fatigue. At present, the problem of alarm fatigue has been listed as a medical injury for many years, and a large number of insignificant alarms reduce the sensitivity of caregivers, thereby bringing clinical risks.

SUMMARY

In order to solve the above problem, the disclosure mainly provides an alarm threshold setting suggestion method, a system, and a monitor, which not only prompt a user to adjust an alarm threshold, but also provide threshold setting suggestion information for user reference, thus being beneficial to relieving the problem of alarm fatigue.

According to a first aspect, an embodiment provides an alarm threshold setting suggestion method, including the following steps:
  obtaining monitoring data of a patient, the monitoring data including at least one of condition information, monitoring parameter information, parameter alarm information and user interaction information;
  determining whether a current alarm threshold associated with a monitoring parameter needs to be adjusted or not according to the monitoring data, and if yes, generating threshold setting suggestion information according to the monitoring data and the current alarm threshold associated with the monitoring parameter; and outputting the threshold setting suggestion information.

According to a second aspect, an embodiment provides a monitoring system, including:
  a display configured to output information;
  a processor configured to execute the following steps:
    obtaining monitoring data of a patient, the monitoring data including at least one of condition information, monitoring parameter information, parameter alarm information and user interaction information; determining whether a current alarm threshold associated with a monitoring parameter needs to be adjusted or not according to the monitoring data, and if yes, generating threshold setting suggestion information according to the monitoring data and the current alarm threshold associated with the monitoring parameter; and controlling the display to output the threshold setting suggestion information.

According to a third aspect, an embodiment provides a monitor, including:
  a sensor for obtaining physiological parameters of a monitored patient to obtain monitoring parameter information;
  an alarm device for sending out a parameter alarm;
  a human-machine interaction device for receiving an input of a user and outputting information; and
  a processor for comparing a monitoring parameter value in the monitoring parameter information with a current alarm threshold associated with a monitoring parameter, and controlling the alarm device to send out a parameter alarm according to a comparison result;
  the processor is also configured to: obtain monitoring data of the patient, the monitoring data including at least one of condition information, monitoring parameter information, parameter alarm information and user interaction information; determine whether the current alarm threshold associated with the monitoring parameter needs to be adjusted or not according to the monitoring data, and if yes, generate a threshold adjusting suggestion according to the monitoring data and the current alarm threshold associated with the monitoring parameter; and display the threshold setting suggestion information on a display interface of the human-machine interaction device.

According to a fourth aspect, an embodiment provides a computer-readable storage medium including a program, the program being executable by a processor to implement the method as mentioned above.

According to the alarm threshold setting suggestion method, the system and the monitor of the above embodiments, monitoring data of a patient is obtained, it is determined whether the current alarm threshold associated with a monitoring parameter needs to be adjusted or not according to the monitoring data, and if yes, threshold setting suggestion information is generated according to the monitoring data and the current alarm threshold associated with the monitoring parameter; and the threshold setting suggestion information is then output. In this way, not only is the user prompted to adjust the alarm threshold, but also the threshold setting suggestion information is provided for user reference, which are beneficial to relieving the problem of alarm fatigue.

DETAILED DESCRIPTION

The disclosure will be further described in detail below through specific implementations in conjunction with the accompanying drawings. Associated similar element reference numerals are used for similar elements in different implementations. In the following embodiments, many details are described such that the disclosure may be better understood. However, it may be effortlessly appreciated by a person skilled in the art that some of the features may be omitted, or may be substituted by other elements, materials, and methods in different cases. In certain cases, some operations involved in the disclosure are not displayed or described in the specification, which is to prevent a core part of the disclosure from being obscured by too much description. Moreover, for a person skilled in the art, the detailed description of the involved operations is not necessary, and the involved operations can be thoroughly understood according to the description in the specification and general technical knowledge in the art.

In addition, the characteristics, operations, or features described in the specification may be combined in any appropriate manner to form various implementations. Meanwhile, the steps or actions in the method description may also be exchanged or adjusted in order in a way that is obvious to a person skilled in the art. Therefore, the various orders in the specification and the accompanying drawings are merely for the purpose of clear description of a certain embodiment and are not meant to be a necessary order unless it is otherwise stated that a certain order must be followed.

The serial numbers themselves for the components herein, for example, "first" and "second", are merely used to distinguish described objects, and do not have any sequential or technical meaning. Moreover, as used in the disclosure, "connection" or "coupling", unless otherwise stated, comprises both direct and indirect connections (couplings).

Figure 1:
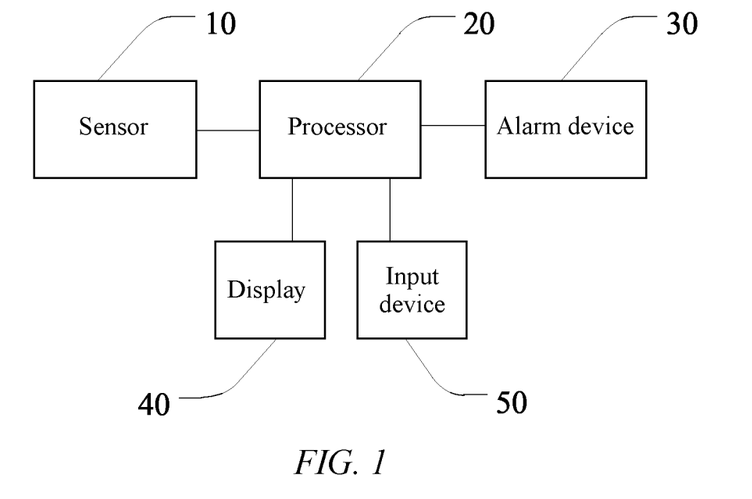
FIG. 1 is a structural block diagram of an embodiment of a monitoring system provided by the disclosure.

The disclosure mainly relates to analyzing monitoring data generated by a monitor, analyzing whether a current alarm threshold associated with a monitoring parameter needs to be adjusted or not, and generating and displaying threshold setting suggestion information for user reference. As shown in FIG. 1, the monitoring system provided by the disclosure includes a processor 20, a display 40, and an input device 50.

The input device 50 is configured to receive an input of a user (typically an operator), for example, one or more of a mouse, a keyboard, a trackball, a joystick, etc. may be used to receive user input instructions, etc. The user may perform an input operation by the input device 50.

The display 40 is configured to output information, such as visualized information. As can be seen, the display 40 and the input device 50 are human-machine interaction devices of the monitoring system, and a touch display may also be used, so that the instructions input by the user can be received, and visualized information can also be displayed.

The processor 20 is configured to obtain monitoring data of a patient, where the monitoring data includes at least one of condition information, monitoring parameter information, parameter alarm information, and user interaction information. The monitoring data may be obtained from a monitor. The processor 20 determines whether a current alarm threshold associated with a monitoring parameter needs to be adjusted or not according to the monitoring data. The alarm threshold may be an upper threshold and/or a lower threshold. For example, a heart rate generally cannot be excessively high or low, so it has upper and lower thresholds. The upper threshold indicates that it is regarded as abnormal when a monitoring parameter value exceeds the upper threshold, triggering an alarm. The lower threshold indicates that it is regarded as abnormal when a monitoring parameter value is less than the lower threshold, triggering an alarm. Only one alarm threshold may be associated with the monitoring parameter, namely, the alarm threshold is only related to the monitoring parameter, irrespective of other monitoring parameters. The numerical unit of such an alarm threshold is usually the same as the numerical unit of the monitoring parameter. Of course, a clinical disease is more complex, and when there may be a plurality of values of monitoring parameters in a specific interval, the deterioration of the patient's condition is reflected and an alarm is required to send out. Thus, there may also be a plurality of types of alarm thresholds associated with monitoring parameters, one is the alarm threshold associated with only one monitoring parameter as described above, and the other is the alarm threshold associated with a plurality of monitoring parameters. The alarm threshold associated with the plurality of monitoring parameters may be, for example, a value calculated by weighting a plurality of monitoring parameter values.

If the current alarm threshold associated with the monitoring parameter needs to be adjusted, the processor 20 generates threshold setting suggestion information according to the monitoring data and the current alarm threshold associated with the monitoring parameter; and the display 40 is controlled to output the threshold setting suggestion information, for example, the display 40 is controlled to display the threshold setting suggestion information. The threshold setting suggestion information may include a suggested alarm threshold for adjustment, for user reference. In this way, not only is the user prompted to adjust the alarm threshold, but also the suggested alarm threshold is provided for user reference, which are beneficial to relieving the problem of alarm fatigue.

The monitoring system provided by the disclosure may be a monitor (such as a bedside monitor), a central station (a central monitoring system), etc., and this embodiment is illustrated by taking the monitor as an example. In this embodiment, the monitor further includes a sensor 10, an alarm device 30, and a storage device (not shown in the figures).

The storage device 30 is configured to store monitoring data.

The sensor 10 is configured to monitor physiological parameters of a patient to obtain monitoring parameter information. The monitoring parameter information includes at least one of a monitoring parameter type (such as one or more of electrocardiograph, respiration, non-invasive blood pressure, blood oxygen saturation, pulse, body temperature, invasive blood pressure, end-tidal carbon dioxide, respiration mechanics, anesthetic gas, cardiac output and bispectral index), a monitoring parameter value, a change trend of the monitoring parameter value, and a parameter alarm switch state, and this embodiment is illustrated by way of example including the four above. The change trend of the monitoring parameter value can reflect whether the patient's condition is deteriorated or kept relatively stable, and the parameter alarm switch state can reflect the attention degree of medical care personnel to the monitoring parameter, so that the information is subsequently used as one of the bases for determining whether the alarm threshold is adjusted or not, and as one of the bases for generating the suggested alarm threshold, and the judgment accuracy can be improved.

The alarm device 30 is configured to send out a parameter alarm to prompt the user that the monitoring parameter value has deviated beyond the alarm threshold. The alarm device may include a buzzer, a loudspeaker, an indicating lamp and/or a display, etc., for example, the buzzer or the loudspeaker sounds an alarm, the indicating lamp flickers, and the display displays the parameter alarm, etc. in the form of a conspicuous color, brightness or font size, which can all prompt the user that the monitoring parameter value is abnormal.

Accordingly, the processor 20 is further configured to compare the monitoring parameter value in the monitoring parameter information with the current alarm threshold associated with the monitoring parameter, and to perform comparison directly in the case where one alarm threshold is associated with one monitoring parameter; and in the case where one alarm threshold is associated with a plurality of monitoring parameters, the processor is further configured to calculate the values of the plurality of associated monitoring parameters according to a preset rule and then compare the values with the alarm threshold. The processor 20 controls the alarm device 30 to send out a parameter alarm according to a comparison result; and in this process, the processor 20 may record parameter alarm information. The parameter alarm information includes at least one of a number of times of a monitoring parameter alarm, a duration of monitoring parameter alarm, an alarm priority, and an acousto-optic setting of a monitoring parameter alarm, and this embodiment is illustrated by way of example including the four above. The alarm priority refers generally to the priority of alarms to be output when there are a plurality of alarms. The acousto-optic setting of the monitoring parameter alarm may be the size of alarm sound, and the flickering frequency, the color or the brightness of the indicating lamp, and may also be the color, the brightness or the font size of content displayed by the display.

Figure 2:
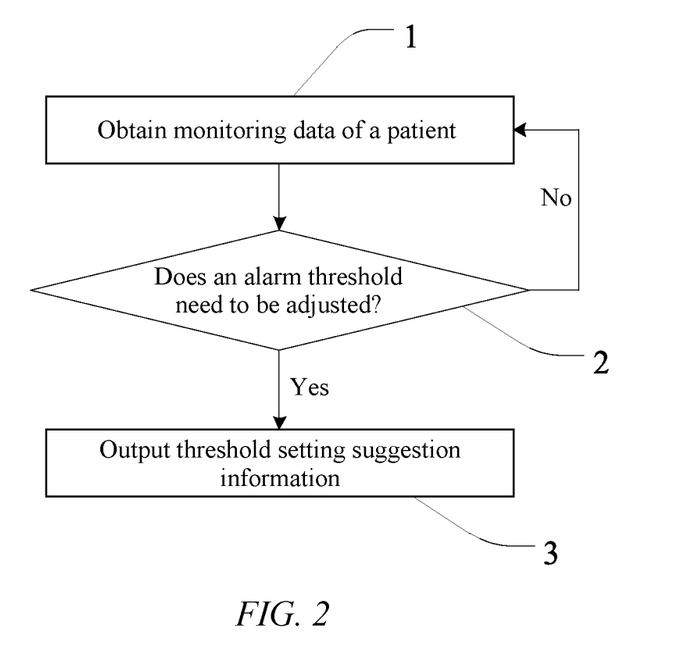
FIG. 2 is a flowchart of an embodiment of an alarm threshold setting suggestion method provided by the disclosure.

In the daily monitoring process, the alarm threshold directly determines the frequency (frequency or the number of times) of an alarm, that is, the number of times of the alarm within unit time. The monitoring system provided by the disclosure may provide the setting suggestion for the monitoring parameter alarm threshold, and the process is shown in FIG. 2 and includes the following steps:

step 1, the processor 20 obtains monitoring data of a patient, for example, the monitoring data is stored in the storage device of the monitor, the processor 20 may obtain the monitoring data from the storage device, the sensor 10 generates monitoring parameter information by monitoring physiological parameters of the patient, and the processor 20 may also obtain the monitoring parameter information from the sensor 10. The monitoring data may include at least one of condition information, monitoring parameter information and parameter alarm information, and the monitoring data may also include user interaction information. This embodiment is illustrated by taking the condition information, the monitoring parameter information, the parameter alarm information and the user interaction information as an example.

The condition information includes at least one of personal characteristic information, disease diagnosis information, a nursing medication record, therapeutic schemes and an electronic medical record, and this embodiment is illustrated by way of example including the five above. The personal characteristic information includes at least one of age, height, weight, and gender of the patient, and this embodiment is illustrated by way of example including the four above. The condition information may be generated in the process of examining, diagnosing and treating the patient by a doctor, and the processor 20 may obtain the condition information from other medical systems and medical devices in network connection to the monitoring system. Of course, the condition information may also be manually input into the system by a doctor and a nurse.

The user interaction information includes: at least one of a monitoring parameter alarm condition set by the user within a monitoring time, an operation of turning on or off a monitoring parameter alarm switch by the user, the number of times and/or the frequency (the number of times and the frequency have essentially the same meaning) of processing a monitoring parameter alarm by the user, and a response time of the user to the monitoring parameter alarm, and this embodiment is illustrated by way of example including the four above. The processor 20 may obtain the user interaction information according to a user's input operation received by an interaction interface displayed by the display 40 and the input device 50. The alarm condition may be an alarm threshold, or may be the condition where the values of which monitoring parameters reach which interval to trigger an alarm, etc.

Step 2, the processor 20 determines whether the current alarm threshold associated with the monitoring parameter needs to be adjusted or not according to the monitoring data, if yes, the processor generates threshold setting suggestion information according to the monitoring data and the current alarm threshold associated with the monitoring parameter, and if not, the processor repeats step 1. For example, the processor 20 determines whether the current alarm threshold associated with the monitoring parameter needs to be adjusted or not according to at least one of the condition information, the monitoring parameter information, the parameter alarm information, and the user interaction information, and if yes, the processor generates the threshold setting suggestion information according to at least one of the current alarm threshold associated with the monitoring parameter, the corresponding condition information, the corresponding monitoring parameter information, the corresponding parameter alarm information and the corresponding user interaction information to reduce the frequency of the parameter alarm. For example, since some conditions may have been accompanied by abnormalities in some monitoring parameters, the number of times of alarms for such monitoring parameters may be reduced.

Step 3, the processor 20 outputs the threshold setting suggestion information, for example, the threshold setting suggestion information is displayed by the display 40 for user reference. The threshold setting suggestion information may include the suggested alarm threshold for adjustment, the user can know that the current alarm threshold needs to be adjusted when seeing the suggested alarm threshold, and can directly use the suggested alarm threshold as a new alarm threshold. Of course, the user may also only refer to the suggested alarm threshold and finally adjust the current alarm threshold according to the judgment of the user himself/herself. While the threshold setting suggestion information is displayed, the current alarm threshold associated with the monitoring parameter, the change trend (such as increasing, decreasing or basically stable) of the monitoring parameter value, etc. may also be displayed for user reference. The threshold setting suggestion information and the current alarm threshold may be directly displayed, or the threshold setting suggestion information and the current alarm threshold may also be displayed when the input device 50 receives a user request for threshold setting suggestion (for example, when an instruction from the user for adjusting the current alarm threshold associated with the monitoring parameter is received), for the user to confirm the suggested alarm threshold or modify the current alarm threshold with reference to the suggested alarm threshold. The threshold setting suggestion information may also include a suggestion to raise the current alarm threshold, a suggestion to lower the current alarm threshold, etc. The threshold setting suggestion information may further include: information suggesting to lower an alarm priority. The threshold setting suggestion information may further include: information suggesting to adjust the acousto-optic setting of the monitoring parameter alarm, for example, it suggests that the user turns down the alarm sound, reduces the flickering frequency of the indicating lamp, dims the indicating lamp, etc., so as to reduce alarm fatigue. In this way, the alarm fatigue can also be alleviated to some extent.

Specifically, the processor 20 may display an alarm threshold adjustment area on a display interface of the display 40 for the user to perform an input operation, the content displayed in the alarm threshold adjustment area includes at least one of the suggested alarm threshold associated with the monitoring parameter, an option for supporting the user to set an alarm threshold, or an option for confirming a suggested alarm threshold, and this embodiment is illustrated by way of example including the three above. In this way, when thinking that the alarm threshold recommended by the system is appropriate, the user can complete modification of the alarm threshold by confirming the suggested alarm threshold by means of the input device 50, that is, after the input device 50 receives a confirmation instruction of the user, the processor 20 takes the suggested alarm threshold as a new current alarm threshold associated with the corresponding monitoring parameter. If the user thinks that the suggested alarm threshold recommended by the system needs to be slightly adjusted, the user may adjust the alarm threshold by the option for supporting the user to set an alarm threshold, that is, after the input device 50 receives an input operation of the user, the processor 20 adjusts the current alarm threshold associated with the monitoring parameter according to the input operation of the user.

Since the monitoring data are different, the method for determining whether the current alarm threshold associated with the monitoring parameter needs to be adjusted or not may also be different. For example, the processor 20 retrieves a preset field in the condition information of the monitoring data, which may be a field reflecting a disease, such as respiratory failure, hypertension, hyperlipaemia. If the preset field is retrieved, it indicates that the patient has the corresponding disease, and the monitoring parameter value corresponding thereto is high or low, which has been usually already known to the doctor, so the number of times of the alarm needs to be decreased, that is, the processor 20 determines that the current alarm threshold of the monitoring parameter associated with the preset field needs to be adjusted. The preset field may be set as required, for example, the preset field may be a preset field reflecting patient diagnosis information. The processor 20 retrieves the preset field reflecting the patient diagnosis information from the condition information of the monitoring data, determines whether the current alarm threshold associated with the monitoring parameter needs to be adjusted or not according to the disease type corresponding to the retrieved preset field, determines that the current alarm threshold needs to be adjusted if the preset field is retrieved, and determines that the adjustment is not needed if the preset field is not retrieved. Taking the "respiratory failure" as an example of the preset field, the processor 20 obtains the patient condition information and retrieves "respiratory failure" from the patient condition information. If the "respiratory failure" is retrieved, it is determined that the current alarm threshold of monitoring parameters such as respiration and blood oxygen saturation needs to be adjusted. If the "respiratory failure" is not retrieved, it is determined that the current alarm threshold for the respiration, the blood oxygen saturation, etc. does not need to be adjusted.

As another example, the processor 20 obtains a monitoring parameter value in a preset first time period from the monitoring parameter information of the monitoring data, obtains an accumulated time when the monitoring parameter is in a preset first range according to the monitoring parameter value in the first time period, and determines whether the current alarm threshold associated with the monitoring parameter needs to be adjusted or not according to the accumulated time. The first range may be a range indicating that the monitoring parameter value is close to the alarm threshold, for example, if the accumulated time exceeds a preset time, it is considered that the monitoring parameter value is close to the current alarm threshold and needs to be adjusted; and if the accumulated time does not exceed the preset time, it is considered that the monitoring parameter value is not close to the current alarm threshold and does not need to be adjusted. The specific values or intervals of the first time period and the first range are set as required. Specifically, in an application, the processor 20 obtains monitoring parameter information, such as a heart rate (HR) value of a patient per second within the past one hour, and determines whether the heart rate value is close to an alarm threshold limit or not. The determining method comprises: calculating a threshold approach limit (namely, a first range), where upper limit=high heart rate alarm limit−5 bpm, and lower limit=low heart rate alarm limit+2 bpm; if the heart rate value is greater than or equal to the upper limit, it is considered that the heart rate at the current second is close to the upper alarm limit; if the heart rate value is less than or equal to the lower limit, it is considered that the heart rate at the current second is close to the lower alarm limit; within the past one hour, t1 represents the accumulated time close to the upper alarm limit, and t2 represents the accumulated time close to the lower alarm limit; if t1>30 minutes, it is considered that the heart rate is "close to the upper alarm limit"; and otherwise, it is considered that the heart rate is "close to the lower alarm limit". Of course, in addition to the accumulated time, other ways of determining whether the monitoring parameter value is close to the alarm threshold or not may also be used. For example, the processor 20 obtains a monitoring parameter value within a preset first time period from the monitoring parameter information of the monitoring data, obtains a quantity of the monitoring parameter value in a preset first range according to the monitoring parameter value within the first time period, and determines whether the current alarm threshold associated with a monitoring parameter needs to be adjusted or not according to the quantity. Specifically, if the quantity exceeds a preset quantity, the processor determines that the monitoring parameter value is close to the alarm threshold, and the current alarm threshold needs to be adjusted; and if not, the current alarm threshold does not need to be adjusted.

For another example, the processor 20 obtains a number of times of a monitoring parameter alarm within a preset second time period from the parameter alarm information of the monitoring data, and determines whether a current alarm threshold associated with a monitoring parameter needs to be adjusted or not according to the number of times of the monitoring parameter alarm within the second time period. The second time period and the first time period may or may not be the same and may be set as desired. Specifically, in an application, the processor 20 obtains the number of times of a "high heart rate" alarm in the past one hour (the number of times of the heart rate exceeding an alarm threshold) from the parameter alarm information, and considers that the current high heart rate "alarm frequently occurs" and determines that the alarm threshold of high heart rate needs to be adjusted if the high heart rate alarm cumulatively occurs five times within the past one hour and at least one high heart rate alarm occurs within the last 15 minutes.

For further example, the processor 20 obtains a number of times and/or frequency of processing a monitoring parameter alarm by the user within a preset third time period from the user interaction information of the monitoring data, and determines whether the current alarm threshold associated with the corresponding monitoring parameter needs to be adjusted or not according to the number of times and/or the frequency of processing the monitoring parameter alarm by the user within the third time period. Specifically, in an application, the processor 20 obtains a number of times of clicking an alarm mute button of the monitor within a time period, such as 20 minutes, from the user interaction information, and if the number of times exceed a preset number of times, the processor determines that the current alarm threshold associated with the corresponding monitoring parameter needs to be adjusted.

Of course, the parameter alarm information and the user interaction information may also be combined to comprehensively determine whether the current alarm threshold needs to be adjusted or not. For example, if the processor 20 obtains that the number of cumulative occurrence times of the high heart rate alarm of the user is three within a time period, such as the past 20 minutes, and that the event that the user clicks the alarm mute button occurs three times, the high heart rate alarm is considered as a "insignificant alarm", and it is determined that the alarm threshold of high heart rate needs to be adjusted. The alarm mute button is a button for canceling the alarm sound of the alarm device 30.

The processor 20 determines whether the current alarm threshold associated with the monitoring parameter needs to be adjusted or not according to the user interaction information, for example, when the user interaction information received by the input device 50 includes an instruction from the user for adjusting the current alarm threshold associated with the monitoring parameter, the processor 20 determines that the current alarm threshold associated with the monitoring parameter needs to be adjusted. For example, the input device 50 may further include a camera, a microphone, etc. The camera, by face recognition, detects that a caregiver (such as a doctor and a nurse) is looking at the monitoring device, and then can determine that the current alarm threshold associated with the monitoring parameter needs to be adjusted; and the microphone collects sound, the processor 20 processes the sound collected by the microphone, recognizes complaints of the caregiver about an alarm by the sound, and determines that the current alarm threshold associated with the monitoring parameter needs to be adjusted. The processor 20 determines that the current alarm threshold associated with the monitoring parameter needs to be adjusted, and then obtains an expectation for change in the number of times of the parameter alarm from the user interaction information, for example, the user processes a monitoring parameter alarm more frequently, indicating that the user desires to reduce the number of times of the alarm, etc. The processor 20 generates a suggested alarm threshold associated with the monitoring parameter according to the expectation for change in the number of times of the parameter alarm and the current alarm threshold associated with the monitoring parameter to meet the expectation for change in the number of times of the parameter alarm. The user interaction information visually reflects the user's expectation, and the number of times of the alarm may need to be reduced, namely, the expectation for change in the number of times of the parameter alarm includes at least reducing the frequency of the parameter alarm.

The processor 20 generating a suggested alarm threshold associated with the monitoring parameter according to the monitoring data and the current alarm threshold of the monitoring parameter may include: if the alarm threshold is the upper threshold, calculating a mean value of the monitoring parameter value in a preset fourth time period, comparing the mean value with the current alarm threshold, increasing the larger of the mean value and the current alarm threshold, for example, increasing the larger of the mean value and the current alarm threshold by a preset value, and taking the increased value as the suggested alarm threshold. The fourth time period and the preset value may be set as required. For example, the processor 20 obtains an alarm threshold upper limit corresponding to a target alarm, such as a high heart rate corresponding to a heart rate alarm upper limit, typically 120 bpm, calculates a suggested alarm threshold, calculates a mean value of the heart rate over the last 15 minutes, and takes the larger of (mean heart rate+10 bpm) and (high heart rate alarm limit+10 bpm) as the suggested alarm threshold. Similarly, if the alarm threshold is the lower threshold, calculating the mean value of the monitoring parameter value in the preset fourth time period, comparing the mean value with the current alarm threshold, reducing the smaller of the mean value and the current alarm threshold, for example, reducing the smaller of the mean value and the current alarm threshold by a preset value, and taking the reduced value as the suggested alarm threshold.

Specifically, in an application, for example, a respiratory failure patient wearing a ventilator frequently or continuously sends out a hypoxemia alarm within a preset first time period, such as an hour, the alarm threshold of a blood oxygen value is adjusted within a certain range (for example, a preset value) according to the blood oxygen value within this time period, and a threshold setting suggestion which can prevent or greatly reduce the hypoxemia alarm is sent out. For example, if a patient frequently or continuously sends out a high heart rate alarm within a time period, such as an hour, or if the heart rate is continuously close to the high threshold of heart rate within a certain range, the alarm threshold of the heart rate is adjusted within a certain range according to a heart rate value within the time period, and a threshold setting which can prevent or greatly reduce the high heart rate alarm is sent out. For example, a patient often or continuously sends out an alarm of high premature ventricular contractions (PVCs) within a time period, such as an hour, then the alarm threshold of PVCs is adjusted within a certain range according to the number of PVCs within the time period and its change trend, and a threshold setting suggestion which can prevent or greatly reduce the alarm of a high PVCs alarm is sent out.

In conclusion, the monitoring system and the method provided by the disclosure determine whether the current alarm threshold associated with the monitoring parameter needs to be adjusted or not, intelligently recommend a threshold adjustment strategy, and assist the user to optimize the alarm threshold and perform other operations, thereby reducing insignificant off-limit alarms, relieving the alarm fatigue, and reducing the harm caused by excessive alarms.

Those skilled in the art may understand that all or some of the functions of the various methods in the above implementations may be implemented by means of hardware or by means of a computer program. When all or some of the functions in the above implementations are implemented by means of a computer program, the program may be stored in a computer-readable storage medium, and the storage medium may comprise: a read-only memory, a random access memory, a magnetic disk, an optical disk, a hard disk, and the like, and the program is executed by a computer to implement the above functions. For example, the program is stored in a memory of an apparatus, and when the program in the memory is executed by means of a processor, all or some of the above functions can be implemented. In addition, when all or some of the functions in the above implementations are implemented by means of a computer program, the program may also be stored in a storage medium such as a server, another computer, a magnetic disk, an optical disk, a flash disk, or a mobile hard disk, may be saved in a memory of a local apparatus through downloading or copying, or version updating may be performed on a system of the local apparatus. When the program in the memory is executed by means of a processor, all or some of the functions in the above implementations can be implemented.

The description has been made with reference to various exemplary embodiments herein. However, those skilled in the art would have appreciated that changes and modifications could have been made to the exemplary embodiments without departing from the scope herein. For example, various operation steps and assemblies for executing operation steps may be implemented in different ways according to a specific application or considering any number of cost functions associated with the operation of the system (for example, one or more steps may be deleted, modified or incorporated into other steps).

In addition, as understood by those skilled in the art, the principles herein may be reflected in a computer program product on a computer-readable storage medium that is pre-installed with computer-readable program codes. Any tangible, non-transitory computer-readable storage medium can be used, including magnetic storage devices (hard disks, floppy disks, etc.), optical storage devices (CD-ROM, DVD, Blu Ray disks, etc.), flash memories, and/or the like. These computer program instructions can be loaded onto a general-purpose computer, a dedicated computer, or other programmable data processing apparatus to form a machine, such that these instructions executed on a computer or other programmable data processing apparatus can generate an apparatus that implements a specified function. These computer program instructions can also be stored in a computer-readable memory that can instruct a computer or other programmable data processing apparatus to operate in a specific manner, such that the instructions stored in the computer-readable memory can form a manufactured product, including an implementation apparatus that implements a specified function. The computer program instructions may also be loaded onto a computer or other programmable data processing apparatus, such that a series of operating steps are executed on the computer or other programmable device to produce a computer-implemented process, such that the instructions executed on the computer or other programmable device can provide steps for implementing a specified function.

Although the principles herein have been shown in various embodiments, many modifications of structures, arrangements, ratios, elements, materials, and components that are particularly suitable for specific environments and operating requirements can be made without departing from the principles and scope of the disclosure. The above modifications and other changes or amendments will be included within the scope herein.

The above specific description has been described with reference to various embodiments. However, those skilled in the art would have appreciated that various modifications and changes could have been made without departing from the scope of the disclosure. Therefore, consideration of the disclosure will be in an illustrative rather than a restrictive sense, and all such modifications will be included within the scope thereof. Likewise, the advantages of various embodiments, other advantages, and the solutions to problems have been described above. However, the benefits, advantages, solutions to problems, and any elements that can produce these, or solutions that make them more explicit, should not be interpreted as critical, necessary, or essential. The term "comprise", "include", and any other variants thereof used herein are non-exclusive, so that the process, method, document, or device that includes a list of elements includes not only these elements, but also other elements that are not explicitly listed or do not belong to the process, method, system, document, or device. Furthermore, the term "coupling" and any other variations thereof used herein refer to physical connection, electrical connection, magnetic connection, optical connection, communication connection, functional connection, and/or any other connection.

Those skilled in the art will recognize that many changes may be made to the details of the above-described embodiments without departing from the basic principles of the disclosure. Therefore, the scope of the disclosure should be determined according to the claims as follows.

The invention claimed is:

1. An automated method for suggesting an alarm threshold setting, performed by a patient monitoring device, comprising:
   obtaining monitoring data of a patient, the monitoring data comprising data of at least one of condition information, monitoring parameter information acquired of the patient by a sensor, parameter alarm information and user interaction information;
   determining, by a processor of the patient monitoring device, whether a current alarm threshold associated with a monitoring parameter needs to be adjusted or not according to the monitoring data while the monitoring parameter is being monitored by the patient monitoring device in real time;
   if it is determined that the current alarm threshold associated with the monitoring parameter needs to be adjusted, generating, by the processor of the patient monitoring device, threshold setting suggestion information according to the monitoring data, the threshold setting suggestion information indicating how the current alarm threshold associated with the monitoring parameter is to be adjusted;
   outputting the threshold setting suggestion information on a display of the patient monitoring device; and if it is determined that the current alarm threshold associated with the monitoring parameter needs not to be adjusted, continuing to obtain the monitoring data of the patient, wherein the condition information comprises at least one of personal characteristic information, disease diagnosis information, a nursing medication record, a therapeutic scheme, and an electronic medical record; the monitoring parameter information comprises at least one of a monitoring parameter type, a monitoring parameter value, a change trend of the monitoring parameter value, and a parameter alarm switch state; the parameter alarm information comprises at least one of a number of times of a monitoring parameter alarm, a duration of a monitoring parameter alarm, an alarm priority, and an acousto-optic setting of a monitoring parameter alarm; and the user interaction information comprises at least one of a monitoring parameter alarm condition set by a user within a monitoring time, an operation of turning on or off a monitoring parameter alarm switch by a user, a number of times and/or a frequency of processing a monitoring parameter alarm by a user, and a response time of a user to the monitoring parameter alarm.

2. The method of claim 1, further comprising:
determining whether the current alarm threshold associated with the monitoring parameter needs to be adjusted or not according to the user interaction information; and
generating a suggested alarm threshold associated with the monitoring parameter according to an expectation for change in a number of times of a parameter alarm indicated in the user interaction information and the current alarm threshold associated with the monitoring parameter, wherein the expectation for change in the number of times of the parameter alarm comprises at least reducing a frequency of the parameter alarm.

3. The method of claim 1, wherein the threshold setting suggestion information comprises: information suggesting to lower an alarm priority, information suggesting to adjust an acousto-optic setting of a monitoring parameter alarm, or a suggested alarm threshold for adjustment.

4. The method of claim 1, wherein outputting the threshold setting suggestion information comprises:
displaying an alarm threshold adjustment area for a user to perform an input operation, content displayed in the alarm threshold adjustment area comprising at least one of a suggested alarm threshold associated with the monitoring parameter, an option for supporting the user to set an alarm threshold, and an option for confirming a suggested alarm threshold; and wherein
the method further comprises:
receiving the input operation of the user, and adjusting the current alarm threshold associated with the monitoring parameter according to the input operation of the user; or after a confirmation instruction of the user is received, taking the suggested alarm threshold as a new current alarm threshold associated with the monitoring parameter.

5. The method of claim 1, wherein the monitoring data comprises at least the user interaction information, and determining whether a current alarm threshold associated with a monitoring parameter needs to be adjusted or not according to the monitoring data comprises:
when the user interaction information contains an instruction from the user for adjusting the current alarm threshold associated with the monitoring parameter, determining that the current alarm threshold associated with the monitoring parameter needs to be adjusted.

6. The method of claim 1, wherein the monitoring data comprises at least the condition information, and determining whether a current alarm threshold associated with a monitoring parameter needs to be adjusted or not according to the monitoring data comprises:
retrieving a preset field in the condition information, and if the preset field is retrieved, determining that the current alarm threshold associated with the preset field needs to be adjusted.

7. The method of claim 1, wherein the monitoring data comprises at least the monitoring parameter information, and determining whether a current alarm threshold associated with a monitoring parameter needs to be adjusted or not according to the monitoring data comprises:
obtaining a monitoring parameter value within a preset time period from the monitoring parameter information, obtaining a quantity of the monitoring parameter value in a preset range or an accumulated time of the monitoring parameter within the preset range according to the monitoring parameter value within the preset time period, and determining whether the current alarm threshold associated with the monitoring parameter needs to be adjusted or not according to the quantity or the accumulated time.

8. The method of claim 1, wherein the monitoring data comprises at least the condition information, and determining whether a current alarm threshold associated with the monitoring parameter needs to be adjusted or not according to the monitoring data comprises:
retrieving a preset field reflecting patient diagnosis information from the condition information of the monitoring data, and determining whether the current alarm threshold associated with the monitoring parameter needs to be adjusted or not according to a disease type corresponding to the retrieved preset field.

9. The method of claim 1, wherein the monitoring data comprises at least the parameter alarm information, and determining whether a current alarm threshold associated with a monitoring parameter needs to be adjusted or not according to the monitoring data comprises:
obtaining a number of times of a monitoring parameter alarm within a preset time period from the parameter alarm information of the monitoring data, and
determining whether a current alarm threshold associated with a monitoring parameter needs to be adjusted or not according to the number of times of the monitoring parameter alarm in the preset time period.

10. The method of claim 1, further comprising: while the threshold setting suggestion information is outputted, outputting the current alarm threshold associated with the monitoring parameter.

11. A patient monitoring system, comprising:
a display configured to output information;
a processor configured to execute the following steps:
obtaining monitoring data of a patient, the monitoring data comprising data of at least one of condition information acquired of the patient by a sensor, monitoring parameter information, parameter alarm information and user interaction information;
determining whether a current alarm threshold associated with a monitoring parameter needs to be adjusted or not according to the monitoring data while the monitoring parameter is being monitored by the patient monitoring device in real time;

if it is determined that the current alarm threshold associated with the monitoring parameter needs to be adjusted, generating threshold setting suggestion information according to the monitoring data, the threshold setting suggestion information indicating how the current alarm threshold associated with the monitoring parameter is to be adjusted;

controlling the display to output the threshold setting suggestion information;

displaying the current alarm threshold associated with the monitoring parameter while displaying threshold setting suggestion information comprising a suggested alarm threshold associated with the monitoring parameter on a display interface of the display, and if it is determined that the current alarm threshold associated with the monitoring parameter needs not to be adjusted, continuing to obtain the monitoring data of the patient, wherein the condition information comprises at least one of personal characteristic information, disease diagnosis information, a nursing medication record, a therapeutic scheme, and an electronic medical record; the monitoring parameter information comprises at least one of a monitoring parameter type, a monitoring parameter value, a change trend of the monitoring parameter value, and a parameter alarm switch state; the parameter alarm information comprises at least one of a number of times of a monitoring parameter alarm, a duration of a monitoring parameter alarm, an alarm priority, and an acousto-optic setting of a monitoring parameter alarm; and the user interaction information comprises at least one of a monitoring parameter alarm condition set by a user within a monitoring time, an operation of turning on or off a monitoring parameter alarm switch by the user, a number of times or a frequency of processing a monitoring parameter alarm by the user, and a response time of the user to the monitoring parameter alarm.

12. The monitoring system of claim 11, wherein the processor is further configured to:
determine whether the current alarm threshold associated with the monitoring parameter needs to be adjusted or not according to the user interaction information; and
generate a suggested alarm threshold associated with the monitoring parameter according to an expectation for change in a number of times of a parameter alarm indicated in the user interaction information and the current alarm threshold associated with the monitoring parameter, wherein the expectation for change in the number of times of the parameter alarm comprises at least reducing a frequency of the parameter alarm.

13. The monitoring system of claim 11, wherein the threshold setting suggestion information comprises: information suggesting to lower an alarm priority, information suggesting to adjust an acousto-optic setting of a monitoring parameter alarm, or a suggested alarm threshold for adjustment.

14. The monitoring system of claim 11, further comprising an input device for receiving the input of the user; the processor is further configured to:
display an alarm threshold adjustment area on a display interface of the display for a user to perform an input operation, content displayed in the alarm threshold adjustment area comprising at least one of a suggested alarm threshold associated with the monitoring parameter, an option for supporting the user to set an alarm threshold, or an option for confirming a suggested alarm threshold; and the processor is further configured to:
adjust the current alarm threshold associated with the monitoring parameter according to the input operation of the user after the input device receives the input operation of the user; or take the suggested alarm threshold as a new current alarm threshold associated with the monitoring parameter after the input device receives the confirmation instruction of the user.

15. The monitoring system of claim 14, wherein the input device is at least one of a mouse, a keyboard, a key, and a display.

16. The monitoring system of claim 11, wherein the monitoring data comprises at least the condition information, and the processor is further configured to:
retrieve a preset field in the condition information, and if the preset field is retrieved, determine that the current alarm threshold associated with the preset field needs to be adjusted; or
retrieve a preset field reflecting patient diagnosis information from the condition information of the monitoring data, and determining whether the current alarm threshold associated with the monitoring parameter needs to be adjusted or not according to the disease type corresponding to the retrieved preset field.

17. The monitoring system of claim 11, wherein the monitoring data comprises at least the monitoring parameter information, and the processor is further configured to:
obtaining a monitoring parameter value within a preset time period from the monitoring parameter information, obtaining a quantity of the monitoring parameter value in a preset range or an accumulated time of the monitoring parameter within the preset range according to the monitoring parameter value within the preset time period, and determining whether the current alarm threshold associated with the monitoring parameter needs to be adjusted or not according to the quantity or the accumulated time.

18. The monitoring system of claim 11, wherein the monitoring data comprises at least the parameter alarm information, and the processor is further configured to:
obtaining a number of times of a monitoring parameter alarm within a preset time period from the parameter alarm information of the monitoring data, and determining whether a current alarm threshold associated with a monitoring parameter needs to be adjusted or not according to the number of times of the monitoring parameter alarm in the preset time period.

* * * * *